US011648067B2

(12) United States Patent
Hashimoto et al.

(10) Patent No.: US 11,648,067 B2
(45) Date of Patent: May 16, 2023

(54) MEDICAL MANIPULATOR AND SURGICAL SYSTEM INCLUDING THE SAME

(71) Applicants: KAWASAKI JUKOGYO KABUSHIKI KAISHA, Kobe (JP); MEDICAROID CORPORATION, Kobe (JP)

(72) Inventors: Yasuhiko Hashimoto, Kobe (JP); Toshiaki Yoshida, Kobe (JP); Wataru Doi, Kobe (JP)

(73) Assignees: KAWASAKI JUKOGYO KABUSHIKI KAISHA, Kobe (JP); MEDICAROID CORPORATION, Kobe (JP)

( * ) Notice: Subject to any disclaimer, the term of this patent is extended or adjusted under 35 U.S.C. 154(b) by 897 days.

(21) Appl. No.: 16/589,144

(22) Filed: Oct. 1, 2019

(65) Prior Publication Data
US 2020/0107890 A1 Apr. 9, 2020

(30) Foreign Application Priority Data
Oct. 5, 2018 (JP) .............................. JP2018-189768

(51) Int. Cl.
*A61B 34/30* (2016.01)
*A61B 34/00* (2016.01)
*A61B 34/35* (2016.01)
*B25J 9/16* (2006.01)

(52) U.S. Cl.
CPC .............. *A61B 34/30* (2016.02); *A61B 34/25* (2016.02); *A61B 34/35* (2016.02); *B25J 9/1689* (2013.01); *A61B 2034/301* (2016.02)

(58) Field of Classification Search
CPC ........................ A61B 1/00147; A61B 1/00149
See application file for complete search history.

(56) References Cited

U.S. PATENT DOCUMENTS

| 2005/0166413 | A1 | 8/2005 | Crampton |
| 2005/0206339 | A1* | 9/2005 | Yoshida ................... G05D 3/12 318/632 |
| 2006/0167440 | A1 | 7/2006 | Cooper et al. |

(Continued)

FOREIGN PATENT DOCUMENTS

| CN | 106236276 A | 12/2016 |
| EP | 2740435 A1 | 6/2014 |

(Continued)

*Primary Examiner* — Martin T Ton
(74) *Attorney, Agent, or Firm* — Metrolex IP Law Group, PLLC

(57) ABSTRACT

A medical manipulator according to one or more embodiments may include: a first manipulator arm with multi-degree of freedom that holds a medical tool at a distal end portion thereof; a second manipulator arm with multi-degree of freedom that holds a medical tool at a distal end portion thereof; an arm base that holds base end portions of the first and second manipulator arms; a movement mechanism configured to move the base end portion of the first manipulator arm with respect to the arm base to change a distance between the base end portion of the first manipulator arm and the base end portion of the second manipulator arm; and a positioner configured to move the arm base and position the arm base in place.

20 Claims, 6 Drawing Sheets

(56) References Cited

U.S. PATENT DOCUMENTS

| | | | |
|---|---|---|---|
| 2009/0082784 A1* | 3/2009 | Meissner | A61B 34/30 606/130 |
| 2010/0224022 A1 | 9/2010 | Choi et al. | |
| 2014/0179997 A1* | 6/2014 | von Grunberg | A61B 1/00149 600/102 |
| 2014/0249546 A1* | 9/2014 | Shvartsberg | A61B 90/50 606/130 |
| 2015/0003945 A1 | 1/2015 | Takahashi et al. | |
| 2017/0000575 A1 | 1/2017 | Griffiths et al. | |
| 2017/0079728 A1* | 3/2017 | Nawrat | A61B 34/30 |
| 2017/0079730 A1 | 3/2017 | Azizian et al. | |
| 2017/0172674 A1 | 6/2017 | Hanuschik et al. | |
| 2017/0172676 A1 | 6/2017 | Itkowitz et al. | |

FOREIGN PATENT DOCUMENTS

| | | | | |
|---|---|---|---|---|
| EP | 3231388 A1 | 10/2017 | | |
| EP | 3520729 A1 | 8/2019 | | |
| JP | 2008-528130 A | 7/2008 | | |
| JP | 2012-5557 A | 1/2012 | | |
| JP | 2012-24920 A | 2/2012 | | |
| JP | 2015-27722 A | 2/2015 | | |
| JP | 2017-515521 A | 6/2017 | | |
| JP | 2017-515522 A | 6/2017 | | |
| WO | 2010/068005 A2 | 6/2010 | | |
| WO | 2013/078529 A1 | 6/2013 | | |
| WO | WO-2018059039 A1* | 4/2018 | | A61B 34/30 |

* cited by examiner

MEDICAL MANIPULATOR AND SURGICAL SYSTEM INCLUDING THE SAME

CROSS REFERENCE TO RELATED APPLICATIONS

This application claims priority to Japanese Patent Application No. 2018-189768 filed on Oct. 5, 2018 and Japanese Patent Application No. 2019-171985 filed on Sep. 20, 2019, the entire contents of which are incorporated herein by reference.

BACKGROUND

The disclosure relates to a medical manipulator and a surgical system including the medical manipulator.

There has been known a master-slave type surgical system that includes multiple manipulator arms and performs surgery by moving the manipulator arms based on operation by a surgeon (for example, see Documents 1, 2, and 3). In such a surgical system, the manipulator arms are arranged close to each other so that the manipulator arms can cooperate to perform a delicate procedure on a surgery site.

In the surgical systems disclosed in Documents 1 and 2, base end portions (support portions) of the manipulator arms are fixed to a platform. On the other hand, in the surgical system disclosed in Document 3, two manipulator arms are attached to an arm base, and the arm base is configured to be moved on a rail.

Document 1: Published Japanese Translation of PCT International Application No. 2017-515522
Document 2: Published Japanese Translation of PCT International Application No. 2008-528130
Document 3: Japanese Patent Application Publication No. 2012-024920

SUMMARY

However, in the surgical systems disclosed in Documents 1 and 2, since the manipulator arms are fixed to the platform, it is difficult to increase the degrees of freedom of the manipulator arms during operation of the manipulator arms depending on the surgical method and urgency level. Additionally, interference between the manipulator arms may occur. In the surgical system disclosed in Document 3, although the manipulator arms can be moved as a group, it is still difficult to increase the degrees of freedom of the manipulator arms, and also the interference between the manipulator arms may occur, as is the case with the other Documents 1 and 2.

An object of an aspect of one or more embodiments may be to provide a medical manipulator that can increase the degrees of freedom of manipulator arms with multi-degree of freedom arranged for a patient and can avoid interference between the manipulator arms with multi-degree of freedom, and a surgical system including the medical manipulator.

A medical manipulator of a first aspect includes: a first manipulator arm with multi-degree of freedom that holds a medical tool at a distal end portion thereof; a second manipulator arm with multi-degree of freedom that holds a medical tool at a distal end portion thereof; an arm base that holds base end portions of the first and second manipulator arms with multi-degree of freedom; a movement mechanism configured to move the base end portion of the first manipulator arm with multi-degree of freedom with respect to the arm base to change a distance between the base end portion of the first manipulator arm with multi-degree of freedom and the base end portion of the second manipulator arm with multi-degree of freedom; and a positioner configured to move the arm base and position the arm base in place.

According to the first aspect, the movement mechanism can change a distance between the base end portion of the first manipulator arm with multi-degree of freedom and the base end portion of the second manipulator arm with multi-degree of freedom. This makes it possible to increase the degrees of freedom of the manipulator arms arranged for a patient depending on the surgical method and urgency level, and to avoid interference between the manipulator arms with multi-degree of freedom. Specifically, it is possible to increase the degrees of freedom of the manipulator arms and to avoid the interference between the manipulator arms with multi-degree of freedom also when the manipulator arms are operated during surgery.

In the first aspect, the medical manipulator may further include: a third manipulator arm with multi-degree of freedom that holds a medical tool at a distal end portion thereof; and a fourth manipulator arm with multi-degree of freedom that holds a medical tool at a distal end portion thereof, wherein the first to fourth manipulator arms with multi-degree of freedom are held by the arm base and arranged in the recited order in a longitudinal direction of the arm base, and the movement mechanism moves a base end portion of the fourth manipulator arm with multi-degree of freedom with respect to the arm base to change a distance between a base end portion of the third manipulator arm with multi-degree of freedom and the base end portion of the fourth manipulator arm with multi-degree of freedom.

According to the above-described configuration, it may be possible to change the distance between the first manipulator arm with multi-degree of freedom and the second manipulator arm with multi-degree of freedom next to each other, and to change the distance between the third manipulator arm with multi-degree of freedom and the fourth manipulator arm with multi-degree of freedom next to each other.

In the first aspect, the arm base may include a base body portion, a first inclined portion that is inclined with respect to a first end portion of the base body portion and connected to the base body portion, and a second inclined portion that is inclined with respect to a second end portion of the base body portion and connected to the base body portion, wherein the first inclined portion holds the first manipulator arm with multi-degree of freedom, the base body portion holds the second and third manipulator arms with multi-degree of freedom, and the second inclined portion holds the fourth manipulator arm with multi-degree of freedom.

According to the above-described configuration, the approach of the manipulator arm with multi-degree of freedom to the patient may be made easy.

In the first aspect, the manipulator arm with multi-degree of freedom may have six or more degrees of freedom.

According to the above-described configuration, it may be easier to avoid the interference between the manipulator arms with multi-degree of freedom, and is easier to approach the manipulator arms with multi-degree of freedom to the patient.

A surgical system of a second aspect includes: a medical manipulator that includes a first manipulator arm with multi-degree of freedom that holds a medical tool at a distal end portion thereof and a second manipulator arm with multi-degree of freedom that holds a medical tool at a distal end portion thereof; and an instruction apparatus that instructs actions of the first and second manipulator arms with multi-degree of freedom, wherein the medical manipulator includes an arm base that holds base end portions of the first and second manipulator arms with multi-degree of freedom, a movement mechanism configured to move the base end portion of the first manipulator arm with multi-degree of freedom with respect to the arm base to change a distance between the base end portion of the first manipulator arm with multi-degree of freedom and the base end portion of the second manipulator arm with multi-degree of freedom, and a positioner configured to move the arm base and position the arm base in place.

According to the second aspect, in the configuration in which the surgical system includes the above-described medical manipulator, the movement mechanism can change the distance between the first manipulator arm with multi-degree of freedom and the second manipulator arm with multi-degree of freedom. This makes it possible to increase the degrees of freedom of the arrangement of the manipulator arms with respect to the patient depending on the surgical method and urgency level, and to avoid the interference between the manipulator arms with multi-degree of freedom. Specifically, it is possible to avoid the interference between the manipulator arms with multi-degree of freedom also when the manipulator arms are operated during surgery.

In the second aspect, the medical manipulator may include an operation input unit that issues an instruction to move the base end portion of the first manipulator arm with multi-degree of freedom with respect to the arm base. In addition, the operation input unit may issue an instruction to move the base end portion of the first manipulator arm with multi-degree of freedom with respect to the arm base during a setup stage before surgery.

According to the configuration, it may be possible to easily change the distance between the arms by the movement mechanism in order to avoid the interference between the arms.

In the second aspect, the movement mechanism may move, during surgery, the base end portion of the first manipulator arm with multi-degree of freedom with respect to the arm base to avoid interference between the first manipulator arm with multi-degree of freedom and the second manipulator arm with multi-degree of freedom.

According to the above-described configuration, it may be possible to easily change the distance between the arms by the movement mechanism in order to avoid the interference between the arms when the first and second arms are operated by a doctor during surgery.

According to the first and second aspects, it may be possible to provide a medical manipulator that can increase the degrees of freedom of manipulator arms with multi-degree of freedom arranged for a patient and can avoid interference between the manipulator arms with multi-degree of freedom, and a surgical system including the medical manipulator.

DETAILED DESCRIPTION

Figure 1:
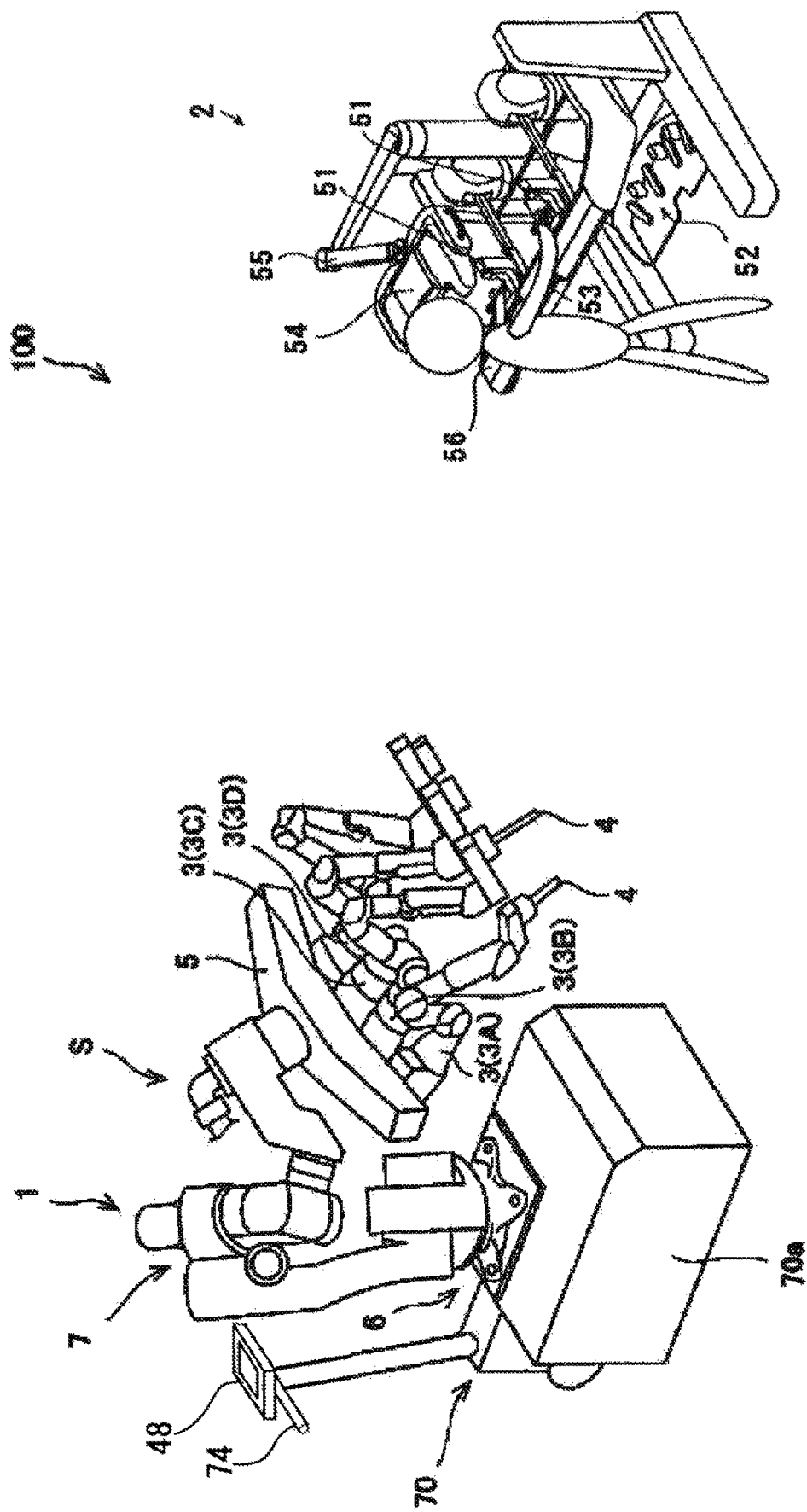
FIG. 1 is a diagram illustrating a perspective view of a surgical system according to one or more embodiments.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

A surgical system according to one or more embodiments is described below with reference to the drawings. The following surgical system according to one or more embodiments is merely an example(s). Thus, the invention is not limited to the following one or more embodiments, and addition, deletion, and modification can be made within the intent of the invention.

As illustrated in FIG. 1, a surgical system 100 is a system fora surgeon such as a doctor to perform endoscopic surgery on a patient with a medical manipulator 1, like robotic-assistant surgery and robotic telesurgery or robotic remote surgery.

The surgical system 100 includes the medical manipulator 1 as a patient-side system and an instruction apparatus 2 for controlling manipulator arms 3 with multi-degree of freedom (hereinafter, simply referred to as arms) of the medical manipulator 1. The instruction apparatus 2 is disposed apart from the medical manipulator 1, and the arms 3 are remotely controlled by the instruction apparatus 2. The surgeon inputs an action to be executed by the manipulator arms 3 to the instruction apparatus 2, and the instruction apparatus 2 transmits the action instruction to the medical manipulator 1. The medical manipulator 1 receives the action instruction transmitted from the instruction apparatus 2. Based on the received action instruction, the medical manipulator 1 operates a medical tool 4 in an elongate shaft shape, such as an endoscope assembly and instrument, held by the arms 3 of the medical manipulator 1.

The instruction apparatus 2 is an apparatus constructing an interface between the surgical system 100 and the surgeon so as to control the arms 3. The instruction apparatus 2 may be disposed inside or outside of a surgery room. The instruction apparatus 2 includes operation manipulator arms 51 to which the surgeon inputs the action instruction, operation pedals 52, a touch panel 53, a monitor 54 displaying an image captured by the endoscope assembly, a support arm 55 supporting the monitor 54 at the height of the face of the operator such as a doctor, a bar 56 on which the touch panel 53 is mounted, and the like. The surgeon operates the operation manipulator arms 51 and the operation pedals 52 to input the action instruction to the instruction apparatus 2 while visually checking an affected area or an involve part through the monitor 54. The action instruction inputted to the instruction apparatus 2 is transmitted to a controller 6 of the medical manipulator 1 through wired or wireless communication. Operation of the arms 3 is controlled by the controller 6. The controller 6 may be formed of a computer such as a microcomputer, for example.

The medical manipulator 1 constructs an interface between the surgical system 100 and the patient. The medical manipulator 1 is disposed inside the surgery room that is sterilized to be a sterile field.

The medical manipulator 1 includes a positioner 7, an elongated arm base 5 attached to a tip end portion or a distal end portion of the positioner 7, and the multiple arms (in this embodiment, four arms) 3 that include base end portions detachably attached to the arm base 5. The medical manipulator 1 is configured to make an accommodation posture in which the arms 3 are folded.

The positioner 7 is formed as a vertical articulated robot and provided on a base body 70a of a wagon 70 disposed at a predetermined location in the surgery room. The positioner 7 can move the position of the arm base 5 three-dimensionally. The positioner 7 and the arm base 5 are covered with not-illustrated sterile drapes and shielded from the sterile field in the surgery room. A touch panel display 48 as an operation input device is provided on a handle 74 of the wagon 70. The touch panel display 48 is configured to display information data related to the state of the medical manipulator 1, information on specific surgery, and information on the entire surgical system 100. In addition, the touch panel display 48 is configured as an input device that receives input of operation of the positioner 7 of the medical manipulator 1.

A distal end portion of an arm 3A out of the arms 3 holds, for example, a replacement instrument (for example, a pair of forceps and so on) as the medical tool 4. A distal end portion of an arm 3B holds an instrument such as a pair of forceps as the medical tool 4, for example. A distal end portion of an arm 3C holds the endoscope assembly as the medical tool 4, for example. A distal end portion of an arm 3D holds a replacement endoscope assembly as the medical tool 4, for example.

In the medical manipulator 1, the arm base 5 has a function as a hub of the arms 3. In this embodiment, the positioner 7 and the arm base 5 form a manipulator arm support body S that movably supports the arms 3. It should be noted that, it is acceptable if the manipulator arm support body S includes at least the arm base 5 without the positioner 7. Such an arm base 5 may be supported by a direct-acting rail, an elevating device, or a bracket attached to a sealing or a wall instead of the positioner 7 to form a manipulator arm support body S.

In the medical manipulator 1, the elements from the positioner 7 to the medical tool 4 are connected in series. Hereinafter, in each of the series of elements in this specification, an end portion close to the positioner 7 is referred to as a base end portion or proximal end portion, and an end portion on the opposite side is referred to as a distal end portion.

Figure 2:
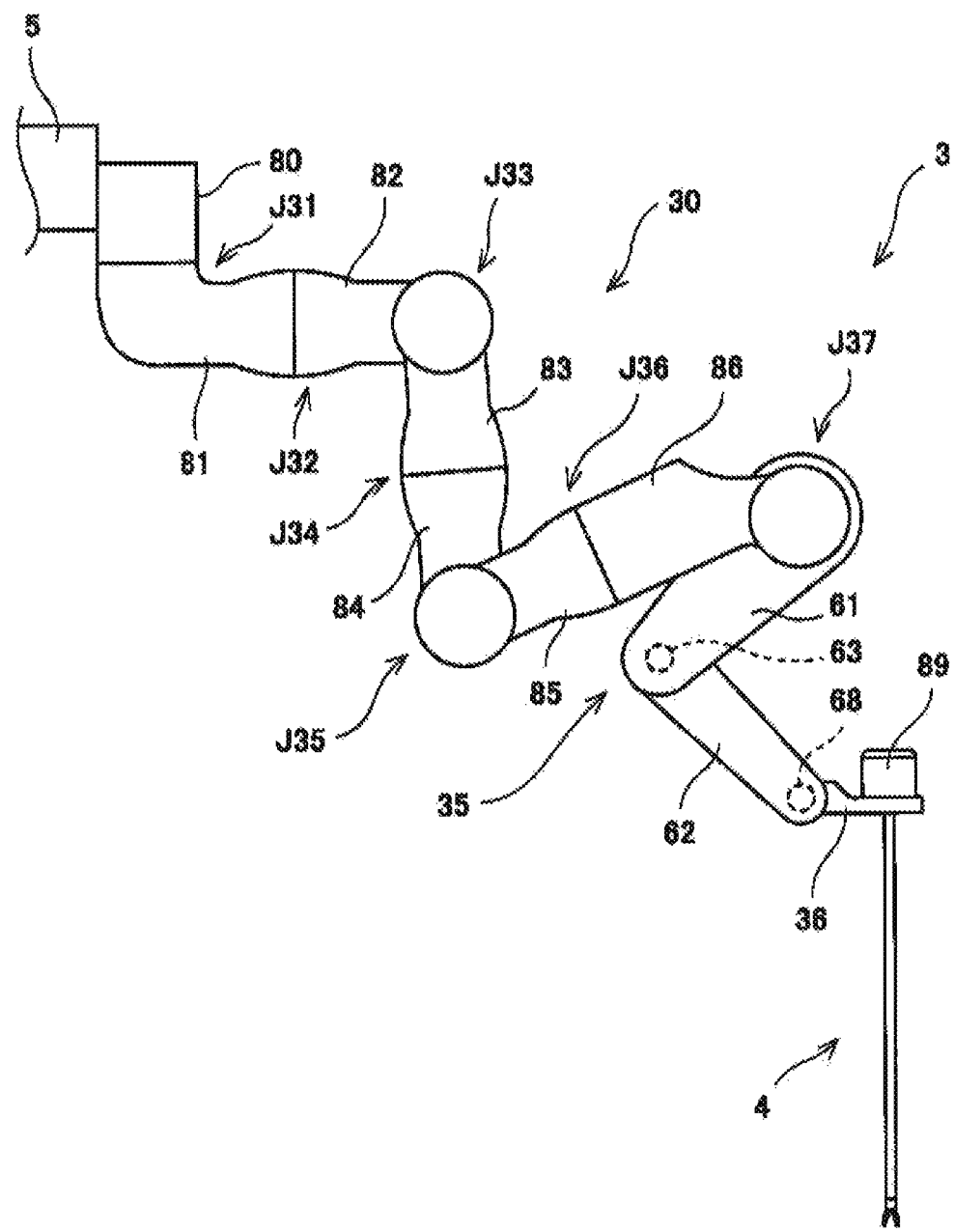
FIG. 2 is a diagram illustrating a view of a configuration of a manipulator arm of a surgical system, such as being illustrated in FIG. 1.

As illustrated in FIG. 2, when the medical tool 4 is an instrument, the medical tool 4 includes a drive unit 89 provided on the base end portion of the medical tool 4. An end effector provided on the distal end portion of the instrument is selected from a group including equipment having a movable joint (for example, pair of forceps, pair of scissors, grasper, needle holder, micro dissector, staple applier, tacker, suction and irrigation tool, snare wire, clip applier, and so on) and equipment having no joints (for example, cutting blade, ablation probe, irrigation device, catheter, suction orifice, and so on).

In the procedure using the medical manipulator 1, first, the controller 6 that receives the action instruction from the touch panel display 48 positions the arm base 5 by moving the positioner 7 so as to put the arm base 5 and a surgical bed or the patient in a predetermined position relationship. Next, the controller 6 positions the medical tool 4 by moving the arms 3 so as to put a sleeve (cannula sleeve) placed on the body surface of the patient and the medical tool 4 in a predetermined initial position relationship. Additionally, the distances between the arms 3 are properly adjusted with the arms 3 slid by the controller 6. The details are described below. The positioning by means of the positioner 7 and the positioning by means of the arms 3 may be performed concurrently. The controller 6 controls, based on the action instruction from the instruction apparatus 2, the arms 3 to operate the medical tool 4 while keeping the positioner 7 still as a general rule, to properly perform displacement and orientation changing of the medical tool 4 for medical procedures.

Next, details of the configuration of each arm 3 are described. As illustrated in FIG. 2, the arm 3 includes an arm body 30 and a translation arm 35 connected to the distal end portion of the arm body 30, and the arm 3 is configured to be capable of moving the distal end portion thereof with respect to the base end portion thereof in a three-dimensional space. In an embodiment illustrated in the drawings, the arms 3 provided to the medical manipulator 1 are all have the same or similar configurations; however, at least one of the arms 3 may have a different configuration from the configurations of the others. A holder 36 capable of holding the medical tool 4 is provided to the distal end portion of the arm 3.

The arm 3 is configured to be attachable to and detachable from the arm base 5. The arm 3 has resistances for cleaning processing and sterile processing, including water resistance, heat resistance, and chemical resistance. There are various ways for the sterile processing of the arm 3. For example, autoclave sterilization, EOG sterilization, chemical sterilization with an antiseptic, and so on may be selectively used.

The arm body 30 includes a base 80 detachably attached to the arm base 5 and a first link 81 to a sixth link 86 connected with one another in order from the base 80 to the distal end portion of the arm 30. More specifically, the base end portion of the first link 81 is connected to the distal end portion of the base 80 with a twist joint J31 arranged therebetween. The base end portion of the second link 82 is connected to the distal end portion of the first link 81 with a twist joint J32 arranged therebetween. The base end portion of the third link 83 is connected to the distal end portion of the second link 82 with a bending joint J33 arranged therebetween. The base end portion of the fourth link 84 is connected to the distal end portion of the third link 83 with a twist joint J34 arranged therebetween. The base end portion of the fifth link 85 is connected to the distal end portion of the fourth link 84 with a bending joint J35 arranged therebetween. The base end portion of the sixth link 86 is connected to the distal end portion of the fifth link 85 with a twist joint J36 arranged therebetween. The base end portion of the translation arm 35 is connected to the distal end portion of the sixth link 86 with a bending joint J37 arranged therebetween. Thus, the arm 3 is formed as a seven-axial joint arm including a redundant axis (in this embodiment, the twist joint J32). In other words, the arm 3 has six or more degrees of freedom. Consequently, the arm 3 can change or transform the posture or the shape thereof without changing the position of the distal end portion of the arm 3.

An outer shell of the arm body 30 is formed of a member that has heat resistance and chemical resistance, such as stainless, for example. Connection portions (or joint portions) between the links are provided with sealing (not illustrated) to provide water resistance. The sealing also has the heat resistance for autoclaved sterilization and chemical resistance for antiseptic. In each connection portion between the links, an end portion of one link is inserted into an end portion of the other link to be connected with the one link, and the sealing is arranged so as to fill the space between the end portions of the links. Thus, the sealing is hidden from external appearance. In this way, entering of water, chemical liquid, and vapor through the space between the sealing and the link is suppressed.

The translation arm 35 moves the holder 36, which is attached to the distal end portion of the translation arm 35, in the axial direction of the medical tool 4, and thus translationally moves the medical tool 4 attached to the holder 36 in the axial direction of the medical tool 4.

The translation arm 35 includes a base end side link 61 that is connected to the distal end portion of the sixth link 86 of the arm body 30 with the bending joint J37 arranged therebetween, a distal end side link 62, a connection shaft 63 connecting the base end side link 61 and the distal end side link 62, and a not-illustrated interlocking mechanism. In addition, a pivot shaft 68 is provided to the distal end portion of the translation arm 35, which is the distal end portion of the distal end side link 62. A drive source of the translation arm 35 is provided to the distal end portion of the arm body 30, or the sixth link 86. The connection shaft 63 is arranged parallel to the bending joint J37, and the distal end side link 62 is configured to be pivotable about the connection shaft 63 with respect to the base end side link 61. A known link mechanism can be employed as the above-mentioned interlocking mechanism. For example, the interlocking mechanism may have a configuration using a pulley and a timing belt and may be a mechanism including a gear train.

A first translation arm drive shaft and a second translation arm drive shaft (both are not illustrated) arranged coaxially with the bending joint J37 are provided to the base end portion of the distal end side link 62 (connection portion between the distal end side link 62 and the sixth link 86). The second translation arm drive shaft is connected to the interlocking mechanism. With the second translation arm drive shaft differentially moving with respect to the first translation arm drive shaft, the translation arm 35 is translated such that the pivot angle of the base end side link 61 about the bending joint J37, the pivot angle of the distal end side link 62 about the connection shaft 63, and the pivot angle of the holder 36 about the pivot shaft 68 are fixed to be in a predetermined ratio (for example, 1:2:1). As the first translation arm drive shaft and the second translation arm drive shaft are synchronized with each other to pivot, the entirety of the translation arm 35 pivots about the bending joint J37 with respect to the arm body 30.

Figure 3:
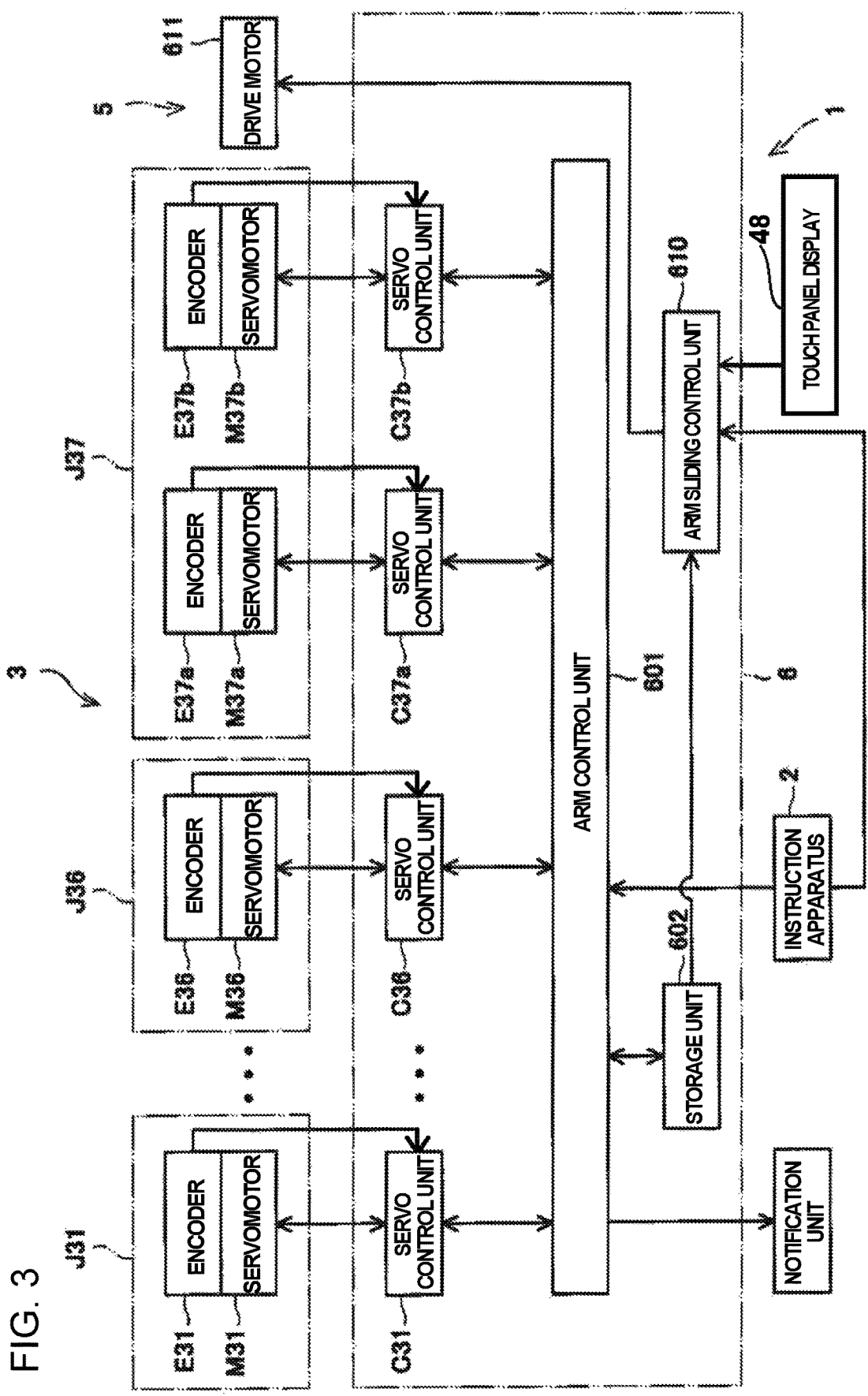
FIG. 3 is a block diagram illustrating a view of a configuration of a control system of a surgical system, such as being illustrated in FIG. 1.

As illustrated in FIG. 3, the arm body 30 is provided with driving servomotors M31 to M36, encoders E31 to E36 detecting the rotation angles of the servomotors M31 to M36, and reduction drives (not illustrated) reducing the outputs of the servomotors M31 to M36 to increase the torque, with each corresponding to the joints J31 to J36. Among the joints J31 to J36 in FIG. 3, the control systems of the twist joint J31 and the twist joint J36 are illustrated as a representative, and the control systems of the other joints J33 to J35 are omitted. In addition, the arm body 30 is provided with a servomotor M37a for driving the first translation arm drive shaft and a servomotor M37b for driving the second translation arm drive shaft, encoders E37a and E37b detecting the rotation angles of the servomotors M37a and M37b, and reduction drives (not illustrated) reducing the outputs of the servomotors M37a and M37b to increase the torque, with each corresponding to the joint J37 that allows the translation arm 35 to perform the translation movement or the pivot movement.

The encoders E31 to E36, E37a, and E37b are provided as an example of rotation position detection units for detecting the rotation positions (rotation angles) of the servomotors M31 to M36, M37a, and M37b. Rotation position detection units such as resolvers may be used instead of the encoders E31 to E36, E37a, and E37b. The above-described elements of the drive systems of the arm 3 and wirings and control units for the elements are made of high-temperature resistant materials and have the heat resistance for sterile processing.

The controller 6 includes an arm control unit 601 that controls movements of the arms 3 (movement other than sliding movement) based on the action instruction and an arm sliding control unit 610 that controls sliding movements of the arms 3. Servo-control units C31 to C36, C37a and C37b are electrically connected to the arm control unit 601, and the servomotors M31 to M36, M37a, and M37b are electrically connected to the arm control unit 601 via not-illustrated amplifier circuits.

Based on the action instruction inputted to the instruction apparatus 2, a position and orientation instruction of the distal end portion of the arm 3 is inputted to the arm control unit 601. Based on the rotation angles detected by the encoders E31 to E36, E37a, and E37b, the arm control unit 601 generates position instruction values and outputs the thus-generated position instruction values. The servo-control units C31 to C36, C37a and C37b receive the position instruction values, and then generate drive instruction values (torque instruction values) based on the rotation angles detected by the encoders E31 to E36, E37a, and E37b and the received position instruction values and output the thus-generated drive instruction values. The amplifier circuits receive the drive instruction values, and then supply drive currents corresponding to the received drive instruction values to the servomotors M31 to M36, M37a, and M37b. As described above, the servomotors M31 to M36, M37a, and M37b are servo-controlled such that the distal end portion of the arm 3 is set at the position and orientation corresponding to the position and orientation instruction.

The controller 6 includes a storage unit 602 that is capable of reading out data to the arm control unit 601. The storage unit 602 stores surgery information that is inputted through the instruction apparatus 2 or the touch panel display 48 in advance.

The storage unit 602 stores information such as the length of the medical tool 4 held by the distal end portion of the arm 3. This allows the arm control unit 601 to grasp the position of the distal end portion of the medical tool 4 held by the distal end portion of the arm 3 based on the position and orientation instruction of the distal end portion of the arm 3. In addition, the storage unit 602 stores processing data for processing of determining the interference between the arms 3.

The arm control unit 601 is configured to control the actions of the arms 3 based on the action instruction from the instruction apparatus 2 during the surgery using the surgical system 100. In this process, the arm control unit 601 uses the above-described processing data stored in the storage unit 602 to perform the processing of determining whether the arms 3 will interfere with each other. In order to avoid the interference, the arm control unit 601 is configured to control the actions of the arms 3 when it is determined that the arms 3 will interfere with each other.

In order to avoid the interference between the arms 3, during the setup stage before the surgery, the arm sliding control unit 610 previously changes the distance between the arms 3 based on the action instruction generated by a surgery assistant operating the touch panel display 48 depending on a condition such as the surgical method. In addition, in order to avoid the interference between the arms 3 during surgery, the arm sliding control unit 610 performs the interference determination processing using the above-described processing data stored in the storage unit 602 based on the action instruction from the instruction apparatus 2 operated by the doctor. The arm sliding control unit 610 is configured to change the distance between the arms 3 to avoid the interference when it is determined that the arms 3 will interfere with each other.

Figure 4:
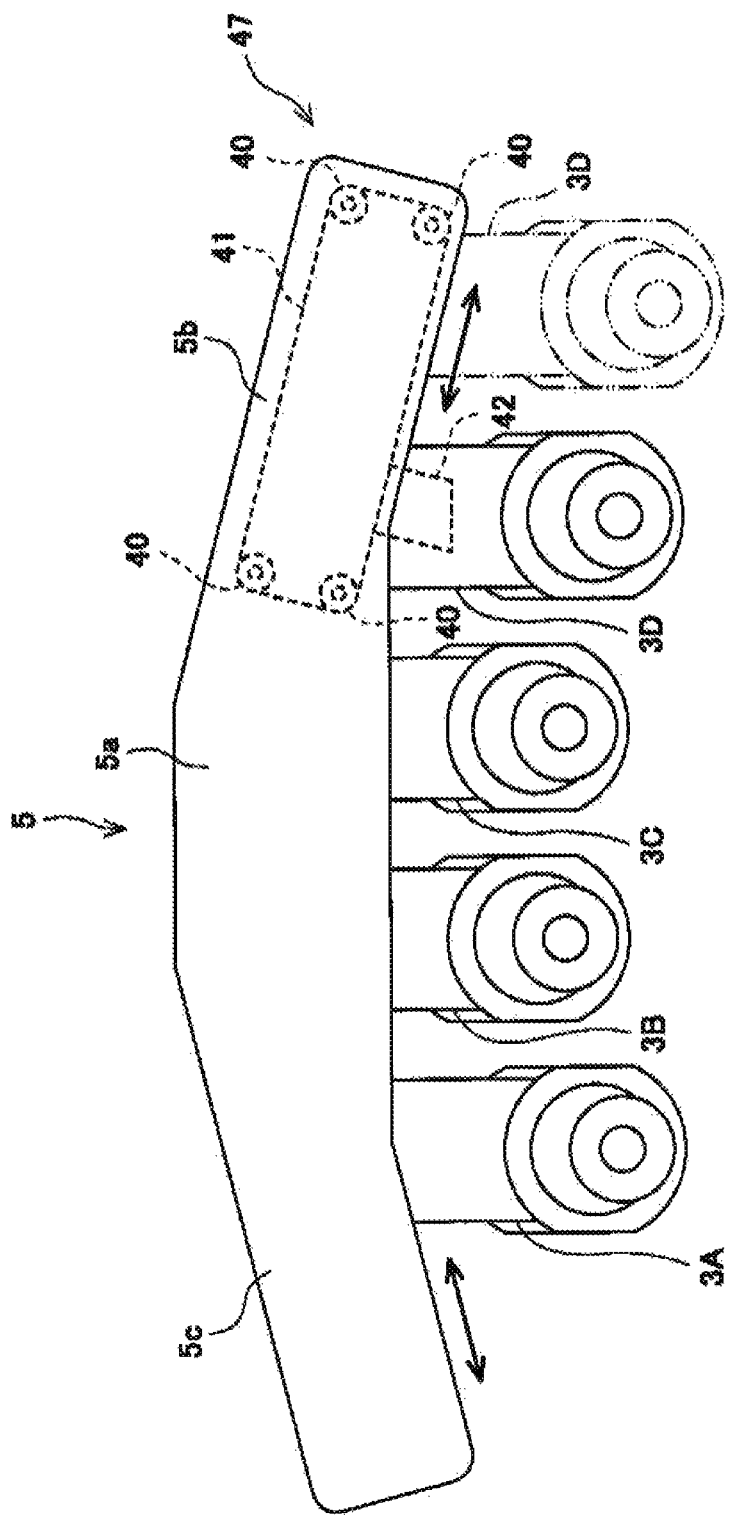
FIG. 4 is a diagram illustrating a front view of a configuration of an arm base, such as being illustrated in FIG. 1.

Next, a configuration of the arm base 5 and a configuration for changing the distance between the arms 3 are described. As illustrated in FIG. 4, the arm base 5 includes a movement mechanism 47. The movement mechanism 47 is configured to change the distance between a base of one arm 3 and a base of another arm 3 next to each other among the four arms 3. The detailed description is given below.

As illustrated in FIG. 4, the arm base 5 is formed in a substantially V-shape in front view. Specifically, the arm base 5 includes an elongated base body portion 5a and long inclined portions 5b and 5c that are connected to and inclined with respect to the base body portion 5a. The inclined portion 5b is integrally connected to one end (right end in FIG. 4) of the base body portion 5a, and the inclined portion 5c is integrally connected to the other end (left end in FIG. 4) of the base body portion 5a. The inclined portion 5b is inclined in a direction closer to the patient when the base body portion 5a is arranged at a position facing the patient. The inclined portion 5c is inclined in the direction closer to the patient when the base body portion 5a is arranged at the position facing the patient. With this configuration, the arm base 5 has a shape that allows the arm base 5 to be placed along the curve of the abdomen of the patient when the arm base 5 is arranged at the position facing the abdomen of the patient.

In this case, in this embodiment, the arm 3B and the arm 3C out of the four arms 3 are fixed to the arm base 5 (base body portion 5a of arm base 5). On the other hand, the arm 3D is provided to the arm base 5 slidably in the inclining direction of the inclined portion 5b, and the arm 3A is provided to the arm base 5 slidably in the inclining direction of the inclined portion 5c. In other words, the arm 3D is configured to be moved in directions closer to and farther from the arm 3C next to the arm 3D, and the arm 3A is configured to be moved in directions closer to and farther from the arm 3B next to the arm 3A.

The arm base 5 is formed like a casing, and the above-described movement mechanism 47 is disposed inside the arm base 5. Specifically, the movement mechanism 47 includes four rollers 40, a sliding belt 41 rotatably installed over the four rollers 40 in a tensioned state, a connection member 42 connecting the sliding belt 41 and the arm 3D, a drive motor 611 (see FIG. 5), and a drive belt 45 (see FIG. 5). In addition, a reduction drive (not illustrated) for reducing the output of the drive motor 611 and an encoder (not illustrated) for detecting the rotation angle of the drive motor 611 are provided.

Figure 5:
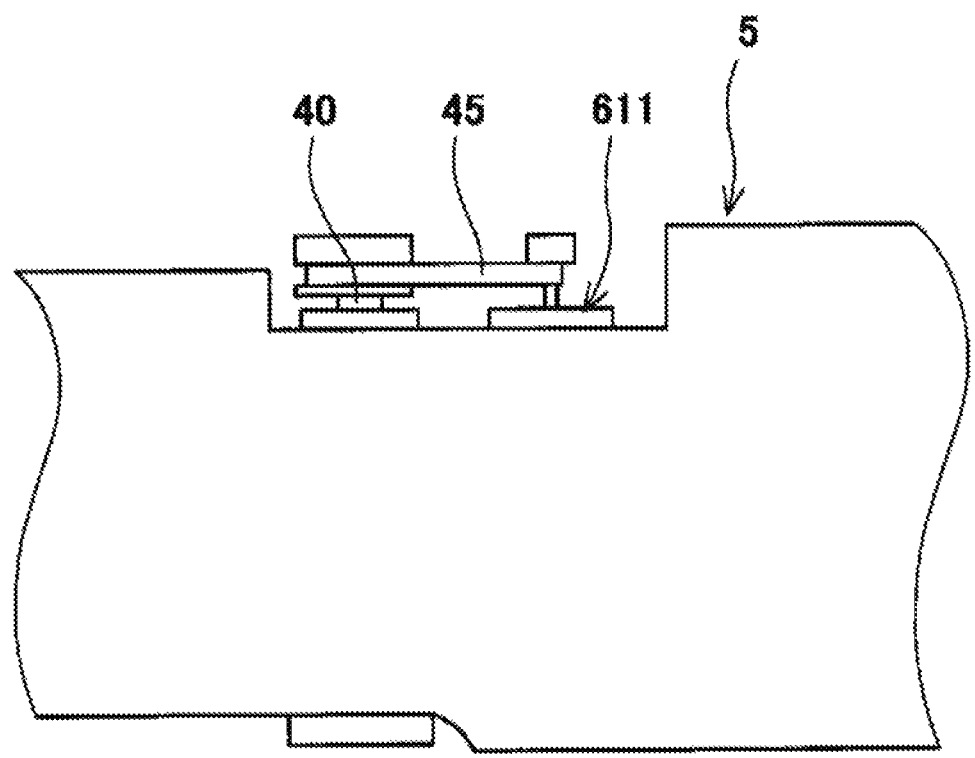
FIG. 5 is a diagram illustrating a plan view of the arm base, such as being illustrated in FIG. 4.

Each roller 40 is arranged at a position of a vertex of a rectangular shape so as to install the sliding belt 41 in a tensioned state in the rectangular shape in front view. The connection member 42 is connected to a part of the sliding belt 41 that is installed over in a tensioned state a pair of the rollers 40 (a pair of the rollers 40 on lower side in FIG. 4) arranged in the inclining direction of the inclined portion 5b. As illustrated in FIG. 5, the drive belt 45 is installed over in a tensioned state a rotation shaft of the drive motor 611 and one of the rollers 40 (a roller 40 on upper left in FIG. 4). In other words, the upper left roller 40 in FIG. 4 is configured as a drive roller, and the other three rollers 40 are configured as driven rollers.

In the above-described configuration, when the distance between the arms 3 is to be changed, the rollers 40 are rotated using the drive belt 45 clockwise or counter-clockwise with the drive motor 611 driven by the arm sliding control unit 610. Thus, the sliding belt 41 is rotated, and thereby the connection member 42 is moved in one side or the other side of the inclining direction of the inclined portion 5b. This allows the arm 3D to be slid along the inclining direction of the inclined portion 5b. Consequently, it is possible to move the arm 3D in the directions closer to and father away from the arm 3C and to change the distance between the arm 3D and the arm 3C. Since a configuration of sliding the arm 3A along the inclining direction of the inclined portion 5c is same as or similar to the configuration of sliding the arm 3D using the movement mechanism 47, additional description is omitted.

As described above, according to the surgical system 100 including the medical manipulator 1 of an embodiment, the movement mechanism 47 can slide the arm 3D to change the distance between the base of the arm 3D and the base of the arm 3C, and can slide the arm 3A to change the distance between the base of the arm 3A and the base of the arm 3B. This makes it possible to increase the degrees of freedom of arrangement of the arms 3 arranged for the patient depending on the surgical method and to avoid the interference between the arms 3.

In an embodiment, the arm base 5 is formed in a substantially V-shaped. This makes the approach of the arms 3 to the patient easy.

In an embodiment, the movement mechanism 47 is configured to allow changing of the distance between the arms 3 during surgery. This makes it possible to change the distance between the arms 3 and to avoid the interference between the arms 3 even when, for example, an unexpected urgent response is required.

Other Embodiments

In addition to the above-described one or more embodiments, the following various modifications can be made without departing from the gist of the invention.

Figure 6A:
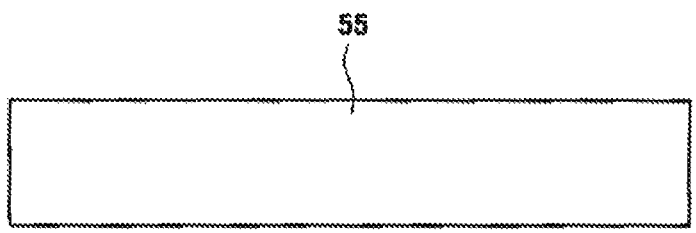
FIG. 6A is a diagram illustrating a front view of a modification of the arm base.
Figure 6B:
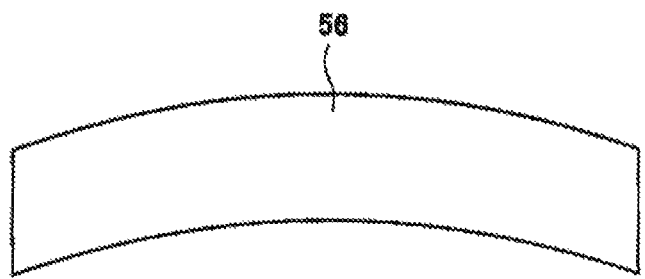
FIG. 6B is a diagram illustrating a front view of another modification of the arm base.

The arm base 5 is formed in a substantially V-shape in front view in the above-described one or more embodiments; however, it is not limited thereto. For example, an arm base 55 formed in a straight line shape in front view as illustrated in FIG. 6A may be employed, or an arm base 56 formed in an arc shape in front view as illustrated in FIG. 6B may be employed. The configuration of FIG. 6B makes the approach of the arm 3 to the patient easy. In addition, the arm base 5 may be formed to be folded at the middle in the longitudinal direction like a mountain shape.

Only the arms 3A and 3D located at the two ends among the four arms 3 are configured to be slidable in the above-described one or more embodiments; however, it is not limited thereto. The four arms 3 may be all configured to be slidable.

The movement mechanism 47 that is configured to slide the arms 3A and 3D using the sliding belt 41 is employed in the above-described one or more embodiments; however, it is not limited thereto. For example, the movement mechanism 47 may be formed of a different actuator, such as a cylinder, or the like.

The invention includes other embodiments in addition to the above-described one or more embodiments without departing from the spirit of the invention. The embodiments are to be considered in all respects as illustrative, and not restrictive. The scope of the invention is indicated by the appended claims rather than by the foregoing descriptions. Hence, all configurations including the meaning and range within equivalent arrangements of the claims are intended to be embraced in the invention.

The invention claimed is:

1. A medical manipulator, comprising:
a first manipulator arm with multiple degrees of freedom that holds a medical tool at a distal end portion thereof;
a second manipulator arm with multiple degrees of freedom that holds a medical tool at a distal end portion thereof;
an arm base that holds base end portions of the first and second manipulator arms;
a movement mechanism configured to move the base end portion of the first manipulator arm with respect to the arm base to change a distance between the base end portion of the first manipulator arm and the base end portion of the second manipulator arm; and
a positioner configured to move the arm base and position the arm base in place, wherein
the movement mechanism comprises a plurality of rollers, a motor that rotates at least one of the rollers and a belt that is suspended on the rollers and moves by rotating at least one of the rollers,
the base end portion of the first manipulator arm is connected to the belt by a connection member, and
the base end portion of the second manipulator arm is fixed to the arm base.

2. The medical manipulator according to claim 1, further comprising:
a third manipulator arm with multiple degrees of freedom that holds a medical tool by a distal end portion thereof; and
a fourth manipulator arm with multiple degrees of freedom that holds a medical tool by a distal end portion thereof, wherein
the first to fourth manipulator arms are held by the arm base and arranged in the recited order in a longitudinal direction of the arm base,
the movement mechanism includes a first movement mechanism that is configured to move the base end portion of the first manipulator arm with respect to the arm base and a second movement mechanism that is configured to move a base end portion of the fourth manipulator arm with respect to the arm base to change a distance between a base end portion of the third manipulator arm and the base end portion of the fourth manipulator arm,
the second movement mechanism comprises a plurality of second rollers, a second motor that rotates at least one of the second rollers and a second belt that is suspended on the second rollers and moves by rotating at least one of the second rollers,
the base end portion of the fourth manipulator arm is connected to the second belt by a second connection member, and
the base end portion of the third manipulator arm is fixed to the arm base.

3. The medical manipulator according to claim 2, wherein
the arm base includes a base body portion, a first inclined portion that is connected to a first end portion of the base body portion which is inclined with respect to the base body portion, and a second inclined portion that is connected to a second end portion of the base body portion which is inclined with respect to the base body portion, wherein
the first inclined portion movably holds the first manipulator arm, the base body portion fixedly holds the second and third manipulator arms, and the second inclined portion movably holds the fourth manipulator arm.

4. The medical manipulator according to claim 3, wherein
the first movement mechanism is arranged in the first inclined portion to move the first manipulator arm with respect to the arm base, and
the second movement mechanism is arranged in the second inclined portion to move the fourth manipulator arm with respect to the arm base.

5. The medical manipulator according to claim 1, wherein each of the first and second manipulator arms has six or more degrees of freedom.

6. The medical manipulator according to claim 1, wherein each of the first and second manipulator arms has seven or more degrees of freedom.

7. The medical manipulator according to claim 1, further comprising
a control unit that controls the movement mechanism to move the base end portion of the first manipulator arm with respect to the arm base to avoid interference between the first manipulator arm and the second manipulator arm during surgery.

8. The medical manipulator according to claim 1, wherein the positioner comprises a vertical articulated robot.

9. The medical manipulator according to claim 1, further comprising:
an operation input unit that issues an instruction to move the base end portion of the first manipulator arm with respect to the arm base.

10. The medical manipulator according to claim 9, wherein
the operation input unit issues an instruction to cause the positioner to move the arm base.

11. The medical manipulator according to claim 1, wherein
the medical manipulator is configured to be transformed in an accommodation posture in which the first and second manipulator arms are folded.

12. A surgical system, comprising:
a medical manipulator that includes a first manipulator arm with multiple degrees of freedom that holds a medical tool by a distal end portion thereof and a second manipulator arm with multiple degrees of freedom that holds a medical tool by a distal end portion thereof; and
an instruction apparatus that instructs actions of the first and second manipulator arms, wherein
the medical manipulator comprises
an arm base that holds base end portions of the first and second manipulator arms,
a movement mechanism configured to move the base end portion of the first manipulator arm with respect to the arm base to change a distance between the base end portion of the first manipulator arm and the base end portion of the second manipulator arm, and a positioner configured to move the arm base and position the arm base in place, wherein the movement mechanism comprises a plurality of rollers, a motor that rotates at least one of the rollers and a belt that is suspended on the rollers and moves by rotating at least one of the rollers, the base end portion of the first manipulator arm is connected to the belt by a connection member, and the base end portion of the second manipulator arm is fixed to the arm base.

13. The surgical system according to claim 12, wherein the medical manipulator includes an operation input unit that issues an instruction to move the base end portion of the first manipulator arm with respect to the arm base.

14. The surgical system according to claim 13, wherein during a setup stage before surgery, the operation input unit issues an instruction to move the base end portion of the first manipulator arm with respect to the arm base.

15. The surgical system according to claim 13, wherein the operation input unit issues an instruction to cause the positioner to move the arm base.

16. The surgical system according to claim 12, further comprising
a control unit that controls the movement mechanism to move the base end portion of the first manipulator arm with respect to the arm base to avoid interference between the first manipulator arm and the second manipulator arm during surgery.

17. The surgical system according to claim 12, further comprising:
a third manipulator arm with multiple degrees of freedom that holds a medical tool at a distal end portion thereof; and
a fourth manipulator arm with multiple degrees of freedom that holds a medical tool at a distal end portion thereof, wherein the first to fourth manipulator arms are held by the arm base and arranged in the recited order in a longitudinal direction of the arm base, the movement mechanism includes a first movement mechanism that is configured to move the base end portion of the first manipulator arm with respect to the arm base and a second movement mechanism that is configured to move a base end portion of the fourth manipulator arm with respect to the arm base to change a distance between a base end portion of the third manipulator arm and the base end portion of the fourth manipulator arm, the second movement mechanism comprises a plurality of second rollers and a second belt that is suspended on the second rollers and moves by rotating the second rollers, the base end portion of the fourth manipulator arm is connected to the second belt by a second connection member, and the base end portion of the third manipulator arm is fixed to the arm base.

18. The surgical system according to claim 17, wherein the arm base includes a base body portion, a first inclined portion that is connected to a first end portion of the base body portion with inclined with respect to the base body portion, and a second inclined portion that is connected to a second end portion of the base body portion with inclined with respect to the base body portion, wherein the first inclined portion movably holds the first manipulator arm, the base body portion fixedly holds the second and third manipulator arms, and the second inclined portion movably holds the fourth manipulator arm.

19. The surgical system according to claim 12, wherein each of the first and second manipulator arms has seven or more degrees of freedom.

20. The surgical system according to claim 12, wherein the positioner comprises a vertical articulated robot.

* * * * *